United States Patent
Sunden

(10) Patent No.: US 12,257,451 B2
(45) Date of Patent: Mar. 25, 2025

(54) MODULAR MICROCLIMATE VETERINARY INCUBATOR

(71) Applicant: Kenneth Clark Sunden, Richland, MI (US)

(72) Inventor: Kenneth Clark Sunden, Richland, MI (US)

( * ) Notice: Subject to any disclaimer, the term of this patent is extended or adjusted under 35 U.S.C. 154(b) by 1042 days.

(21) Appl. No.: 17/248,281

(22) Filed: Jan. 18, 2021

(65) Prior Publication Data

US 2021/0220201 A1     Jul. 22, 2021

Related U.S. Application Data

(60) Provisional application No. 62/962,536, filed on Jan. 17, 2020.

(51) Int. Cl.
*A61N 5/06* (2006.01)
*A61D 99/00* (2006.01)

(52) U.S. Cl.
CPC ........... *A61N 5/0625* (2013.01); *A61D 99/00* (2013.01); *A61N 2005/0659* (2013.01)

(58) Field of Classification Search
CPC .................................................. A61N 5/0625
USPC ..... 119/302–328; 220/4.29–8, 602, 662, 665
See application file for complete search history.

(56) References Cited

U.S. PATENT DOCUMENTS

| | | | | | |
|---|---|---|---|---|---|
| 936,451 | A | * | 10/1909 | Havenhill | A47F 5/005 217/65 |
| 1,126,258 | A | * | 1/1915 | Myers | A47F 3/12 312/137 |
| 1,322,161 | A | * | 11/1919 | Calow | H05B 1/0272 219/390 |
| 1,328,032 | A | * | 1/1920 | Calow | A01K 41/00 119/319 |

(Continued)

FOREIGN PATENT DOCUMENTS

| | | | | | |
|---|---|---|---|---|---|
| CN | 106922567 | A | * | 7/2017 | ............ A01K 41/00 |
| CN | 107087315 | A | * | 8/2017 | |

(Continued)

OTHER PUBLICATIONS

Merged translation of JP-2002051657-A (Year: 2002).*

(Continued)

*Primary Examiner* — Morgan T Jordan
(74) *Attorney, Agent, or Firm* — Squire Patent Consulting & IP Law LLC; Brendan E. Squire

(57) ABSTRACT

A veterinary incubator features a modular hygienic design, with a ceramic infrared heating element. The ceramic infrared heating element heats a puppy more deeply and can be tailored to the specific condition of the puppy, allowing for better processing of colostrum and food—leading to a better weight gain, a stronger immune system and eyes opening sooner than conventional incubators with puppies from the same litter. The veterinary incubator can be fully disassembled with 100% user replaceable modular components to (Continued)

allow for more effective disinfecting and elimination of service calls. The veterinary incubator creates a microenvironment that compliments a small animal's ability to seek out warmer and cooler parts of their environment to regulate body temperature and can be adjusted to allow for only good choices based upon the small animal's condition.

14 Claims, 4 Drawing Sheets

(56) References Cited

U.S. PATENT DOCUMENTS

| | | | | |
|---|---|---|---|---|
| 1,338,404 | A * | 4/1920 | St Clair | A01K 41/00 119/309 |
| 1,393,531 | A * | 10/1921 | Howard, Sr. | A01K 41/00 219/400 |
| 1,413,887 | A * | 4/1922 | Baba | H05B 1/0216 219/407 |
| 1,432,827 | A * | 10/1922 | Bauer | A01K 63/003 220/668 |
| 1,890,236 | A * | 12/1932 | Rookstool | A01K 41/00 219/400 |
| 1,981,710 | A * | 11/1934 | Rix | E06B 5/006 312/265.5 |
| 2,252,191 | A | 8/1941 | Marks | |
| 2,267,244 | A * | 12/1941 | Markey | A01K 41/00 119/319 |
| 2,356,930 | A * | 8/1944 | Horstkotte | D06F 57/08 211/170 |
| 2,358,081 | A * | 9/1944 | Marick | A01K 31/19 219/541 |
| 2,385,954 | A * | 10/1945 | Tarnopol | B65D 13/02 422/240 |
| 2,627,841 | A | 2/1953 | Johnson | |
| 2,646,930 | A | 7/1953 | Dryden | |
| 2,909,152 | A * | 10/1959 | Cordis | A01K 31/19 119/309 |
| 2,940,760 | A * | 6/1960 | Brinkman, Jr. | A63F 9/12 273/288 |
| 2,985,137 | A * | 5/1961 | Horne | A01K 31/19 119/307 |
| 2,989,226 | A * | 6/1961 | Swartz | B65D 11/188 229/117.02 |
| 3,062,941 | A * | 11/1962 | White | G05D 23/24 236/DIG. 14 |
| 3,096,428 | A * | 7/1963 | Dublirer | A01K 1/0158 392/432 |
| 3,106,801 | A * | 10/1963 | Risacher | A01G 9/16 219/385 |
| 3,139,881 | A * | 7/1964 | Fannon, Jr. | A01K 31/20 126/92 R |
| 3,228,736 | A * | 1/1966 | Beckerman | F16B 12/02 220/668 |
| 3,237,599 | A * | 3/1966 | Torrey | A01K 1/031 119/419 |
| 3,299,253 | A * | 1/1967 | Lawson, Jr. | H05B 3/342 219/385 |
| 3,316,041 | A * | 4/1967 | Nelson | A47F 3/005 220/668 |
| 3,321,864 | A * | 5/1967 | Stasiuk | A01G 9/20 47/19.1 |
| 3,376,405 | A * | 4/1968 | Gower, III | G05D 23/24 219/385 |
| 3,399,654 | A * | 9/1968 | Schroer | A01K 1/0613 119/752 |
| 3,429,297 | A * | 2/1969 | Schroer | A01K 23/005 119/417 |
| 3,516,389 | A * | 6/1970 | Meyer | A01K 15/00 446/124 |
| 3,536,044 | A * | 10/1970 | Branam | A01K 1/031 119/481 |
| 3,543,726 | A * | 12/1970 | Marsh | A01K 41/00 119/319 |
| 3,584,927 | A * | 6/1971 | Ott | A01K 1/031 47/16 |
| 3,667,648 | A * | 6/1972 | Koziol | A47J 36/06 126/211 |
| 3,677,433 | A * | 7/1972 | Collins | B65D 7/32 220/4.01 |
| 3,699,926 | A * | 10/1972 | Stockl | A01K 1/0157 206/0.8 |
| 3,712,268 | A * | 1/1973 | Reed | G05D 23/1934 219/385 |
| 3,779,210 | A | 12/1973 | Blair | |
| 3,803,571 | A * | 4/1974 | Luz | A01K 29/005 377/16 |
| 3,856,177 | A * | 12/1974 | Fudge | A62C 13/78 70/95 |
| 3,912,111 | A * | 10/1975 | Marengoni | A47F 3/005 220/4.01 |
| 3,955,702 | A * | 5/1976 | Lundy | F21S 8/088 220/4.28 |
| 4,016,833 | A * | 4/1977 | Ray | A01K 1/03 119/498 |
| 4,036,177 | A * | 7/1977 | DeSmit | A01K 1/031 119/457 |
| 4,191,174 | A | 3/1980 | Martin | |
| 4,201,153 | A | 5/1980 | Nace | |
| 4,292,929 | A | 10/1981 | Tellers | |
| 4,340,859 | A * | 7/1982 | Farley | G01R 31/50 119/319 |
| 4,365,590 | A * | 12/1982 | Ruggieri | A01K 1/031 119/418 |
| 4,448,150 | A * | 5/1984 | Catsimpoolas | A01K 1/031 250/221 |
| 4,495,892 | A | 1/1985 | Jodar et al. | |
| 4,526,133 | A * | 7/1985 | LoMaglio | A01K 1/031 119/419 |
| 4,678,569 | A * | 7/1987 | Cunningham | A01K 59/04 210/187 |
| 4,750,474 | A | 6/1988 | Dukhan et al. | |
| 5,036,795 | A * | 8/1991 | Houghton | A01K 1/031 52/127.6 |
| 5,090,617 | A * | 2/1992 | Swan | A01K 41/00 236/3 |
| 5,092,268 | A * | 3/1992 | Taylor | A01K 61/60 261/81 |
| 5,119,467 | A * | 6/1992 | Barsky | H05B 3/26 338/308 |
| 5,140,947 | A | 8/1992 | Bruce | |
| 5,267,941 | A | 12/1993 | Snyders | |
| 5,300,105 | A * | 4/1994 | Owens | A61F 7/02 607/114 |
| 5,385,118 | A * | 1/1995 | Coiro, Sr. | A01K 1/031 119/417 |
| 5,419,628 | A * | 5/1995 | Myslinski, Jr. | F16B 12/125 312/109 |
| 5,473,845 | A * | 12/1995 | Livingston | E04H 1/1205 52/79.9 |
| 5,572,952 | A * | 11/1996 | Manome | A01K 63/02 119/203 |
| 5,749,321 | A * | 5/1998 | Ikuse | A01K 1/031 119/458 |
| 5,803,018 | A * | 9/1998 | Liou | A01K 31/07 119/474 |
| 5,823,143 | A | 10/1998 | Wilson | |
| 5,915,072 | A * | 6/1999 | Campbell | A61G 11/00 392/408 |
| 5,950,615 | A * | 9/1999 | Anderson | F24C 1/10 119/305 |
| 6,318,295 | B1 * | 11/2001 | Wade | A01K 1/033 119/500 |
| 6,352,076 | B1 * | 3/2002 | French | A61D 7/04 119/420 |
| 6,425,347 | B1 | 7/2002 | Bogner et al. | |
| 6,568,350 | B1 * | 5/2003 | Savard | A01K 1/034 119/458 |

(56) References Cited

U.S. PATENT DOCUMENTS

| | | | |
|---|---|---|---|
| 6,725,805 B1 | 4/2004 | Bach | |
| 7,134,404 B2 | 11/2006 | Slone | |
| 7,487,744 B1* | 2/2009 | Goldberg | A01K 31/07 |
| | | | 119/482 |
| 8,438,995 B1* | 5/2013 | Donahue | A01K 1/00 |
| | | | 119/512 |
| 8,795,151 B2* | 8/2014 | Falk | A61G 11/00 |
| | | | 128/920 |
| 9,198,402 B2 | 12/2015 | Santo | |
| 9,675,040 B2* | 6/2017 | Cleary | A01K 63/06 |
| 9,913,454 B2 | 3/2018 | Van Buuren | |
| D814,719 S | 4/2018 | Bae | |
| 10,021,858 B1 | 7/2018 | Packard | |
| 2002/0148410 A1* | 10/2002 | Thomas | A01K 63/065 |
| | | | 119/452 |
| 2004/0144328 A1* | 7/2004 | Bonner | A01K 1/032 |
| | | | 119/455 |
| 2006/0236951 A1* | 10/2006 | Gabriel | A01K 1/031 |
| | | | 119/455 |
| 2006/0260972 A1* | 11/2006 | Ayres | A01K 1/034 |
| | | | 206/512 |
| 2007/0000447 A1* | 1/2007 | Jakubowski | A01K 31/08 |
| | | | 119/453 |
| 2007/0294819 A1* | 12/2007 | Levesque | A61H 33/066 |
| | | | 392/416 |
| 2008/0046044 A1* | 2/2008 | Jahnigen | A61N 5/06 |
| | | | 606/27 |
| 2008/0236510 A1* | 10/2008 | Silverman | A01K 31/08 |
| | | | 206/509 |
| 2008/0266115 A1* | 10/2008 | Labrecque | A01K 1/0076 |
| | | | 340/573.3 |
| 2009/0159011 A1* | 6/2009 | Santo | A01K 41/023 |
| | | | 312/236 |
| 2010/0168502 A1 | 7/2010 | Delaporte et al. | |
| 2012/0085293 A1* | 4/2012 | Owens | A01K 1/03 |
| | | | 119/455 |
| 2012/0125264 A1* | 5/2012 | Veng | A01K 29/005 |
| | | | 119/416 |
| 2012/0209360 A1* | 8/2012 | Dunlop | A61F 7/0097 |
| | | | 607/107 |
| 2014/0251228 A1* | 9/2014 | Jensen-Jarolim | A61B 5/01 |
| | | | 119/421 |
| 2016/0044892 A1* | 2/2016 | Hahn | A01K 1/031 |
| | | | 119/455 |
| 2017/0135311 A1* | 5/2017 | Driver | A61M 16/1005 |
| 2018/0216833 A1* | 8/2018 | Baker | F24C 15/04 |

FOREIGN PATENT DOCUMENTS

| | | | | |
|---|---|---|---|---|
| DE | 10135340 A1 | * | 2/2003 | A61D 11/00 |
| DE | 202014002845 U1 | * | 6/2014 | A01K 1/02 |
| JP | 2002051657 A | * | 2/2002 | |
| KR | 200341304 Y1 | * | 2/2004 | |
| KR | 100755129 B1 | * | 9/2007 | |
| KR | 100824348 B1 | * | 4/2008 | |
| KR | 20160000715 A | * | 1/2016 | |
| WO | WO-2005023662 A1 | * | 3/2005 | B65D 11/1873 |
| WO | WO-2006096118 A1 | * | 9/2006 | A01K 1/0157 |

OTHER PUBLICATIONS

Merged translation of DE-10135340-A1 (Year: 2003).*
Merged translation of KR-200341304-Y1 (Year: 2004).*
Merged translation of WO-2005023662-A1 (Year: 2005).*
Merged translation of WO-2006096118-A1 (Year: 2006).*
Merged translation of KR-100755129-B1 (Year: 2007).*
Merged translation of KR-100824348-B1 (Year: 2008).*
Merged translation of DE-202014002845-U1 (Year: 2014).*
Merged translation of KR-20160000715-A (Year: 2016).*
Merged translation of CN-106818494-A (Year: 2017).*
Merged translation of CN-106922567-A (Year: 2017).*
Merged translation of CN-107087315-A (Year: 2017).*
Large Puppy Warmer from puppywarmer.com available at <http://web.archive.org/web/20181209234130/http://www.puppywarmer.com/default.asp> (Year: 2018).*
Large Puppy Warmer from puppywarmer.com available at <http://web.archive.org/web/20181223135452/http://www.puppywarmer.com/product-p/pw18x18.htm> (Year: 2018).*
"Ceramic Infrared Heating Elements" https://web.archive.org/web/20200921154857/https://www.ceramicx.com/products/ceramic-elements/ (Year: 2020).*

* cited by examiner

MODULAR MICROCLIMATE VETERINARY INCUBATOR

CROSS-REFERENCE TO RELATED APPLICATION

This application claims the benefit of priority of U.S. provisional application No. 62/962,536, filed Jan. 17, 2020, the contents of which are herein incorporated by reference.

BACKGROUND OF THE INVENTION

The present invention relates to incubators, and more particularly to incubators used in veterinary practice.

It is estimated that 16 to 20% of newborn puppies die in the first three weeks of life in the United States. These deaths are due to a variety of factors, including: inability to regulate body temperature, oxygen deprivation as a result of difficult birth, premature birth, small for gestational age, immature lung development, dehydration, bacterial infections and viral infections.

Other veterinary incubation systems do not provide precise environmental controls, and require a service call to replace a sensor, controller or a heater. These other systems cannot be disassembled to have key components manually disinfected, autoclaved or run through a devise to use water or steam in excess of 140° F. for purposes of sterilizing—leaving corners and other shapes that are difficult to disinfect. Likewise, these systems extensively use plastic which can release harmful chemicals when heated. Similarly, these systems use infrared heaters that output light, which can result in less effective sleep of a small animal.

As can be seen, there is a need for an improved veterinary incubator that provides a controlled microclimate for newborn puppies to significantly enhance survival rates.

SUMMARY OF THE INVENTION

In one aspect of the present invention, a microclimate veterinary incubator, is disclosed. The microclimate veterinary incubator includes a plurality of tempered glass panels dimensioned to form an incubator enclosure, when assembled. A plurality of corner brackets, each configured to join and retain the plurality of tempered glass panels as an assembled incubator enclosure. A thermal mat is dimensioned for placement spanning a bottom of the assembled incubator enclosure. The thermal mat having a surface to capture a thermal radiation. A heating element is configured to be coupled within the assembled incubator enclosure and project an infrared heat source onto a surface the thermal mat to define a thermal gradient on the surface of the thermal mat and an airspace above the thermal mat.

In some embodiments, a controller is configured to control the heating element to maintain the thermal gradient at a desired temperature set point.

In some embodiments, a plurality of thermal sensors are configured to be coupled to one or more of the plurality of tempered glass panels and oriented to measure a temperature of the airspace above the thermal mat. The plurality of thermal sensors operably coupled to the controller.

In some embodiments, a reflective shroud is dimensioned to surround the heating element and focus the infrared heat source at a center of the thermal gradient.

In some embodiments, a plurality of upstanding protrusions are defined on an upper surface of the thermal mat in a spaced apart pattern spanning the upper surface of the thermal mat.

In some embodiments, the corner bracket includes three orthogonal faces defining a corner of a regular rectangular enclosure. An aperture is defined in each of the three orthogonal faces.

In some embodiments, the plurality tempered glass panels include a top panel, a bottom panel, a side panel, a rear panel, and a front panel. The front panel may include a fenestration and a door panel movable to close the fenestration.

In other embodiments, the side panel may include a secondary fenestration. An access panel is operably coupled to the side panel to selectively close the secondary fenestration.

In other aspects of the invention, a microclimate veterinary incubator is disclosed. The microclimate veterinary incubator includes a plurality of tempered glass panels dimensioned to form an incubator enclosure. The plurality of tempered glass panels includes a top panel, a bottom panel, front panel, a rear panel, and a side panel. A plurality of corner brackets joins and retain the plurality of tempered glass panels as the incubator enclosure. A thermal mat is supported at bottom of the incubator enclosure spanning between the front panel, the back panel, and the side panel. The thermal mat has a surface to capture a thermal radiation. A heating element is removably attached to the top panel and extends into an interior of the incubator enclosure. The heating element is configured to project an infrared heat source onto a surface the thermal mat to define a thermal gradient on the surface of the thermal mat and an airspace above the thermal mat.

In some embodiments, a controller is configured to control the heating element to maintain the thermal gradient at a desired temperature set point. At least one thermal sensor is coupled to one or more of the plurality of tempered glass panels and oriented to measure a temperature of the airspace above the thermal mat. The at least one thermal sensor are operably coupled to the controller.

In some embodiments, a reflective shroud surrounds the heating element. The thermal shroud has a focal length to focus the infrared heat source at a center of the thermal gradient.

In some embodiments, a plurality of upstanding protrusions are defined on an upper surface of the thermal mat in a spaced apart pattern spanning the upper surface of the thermal mat.

These and other features, aspects and advantages of the present invention will become better understood with reference to the following drawings, description and claims.

DETAILED DESCRIPTION

Figure 1:
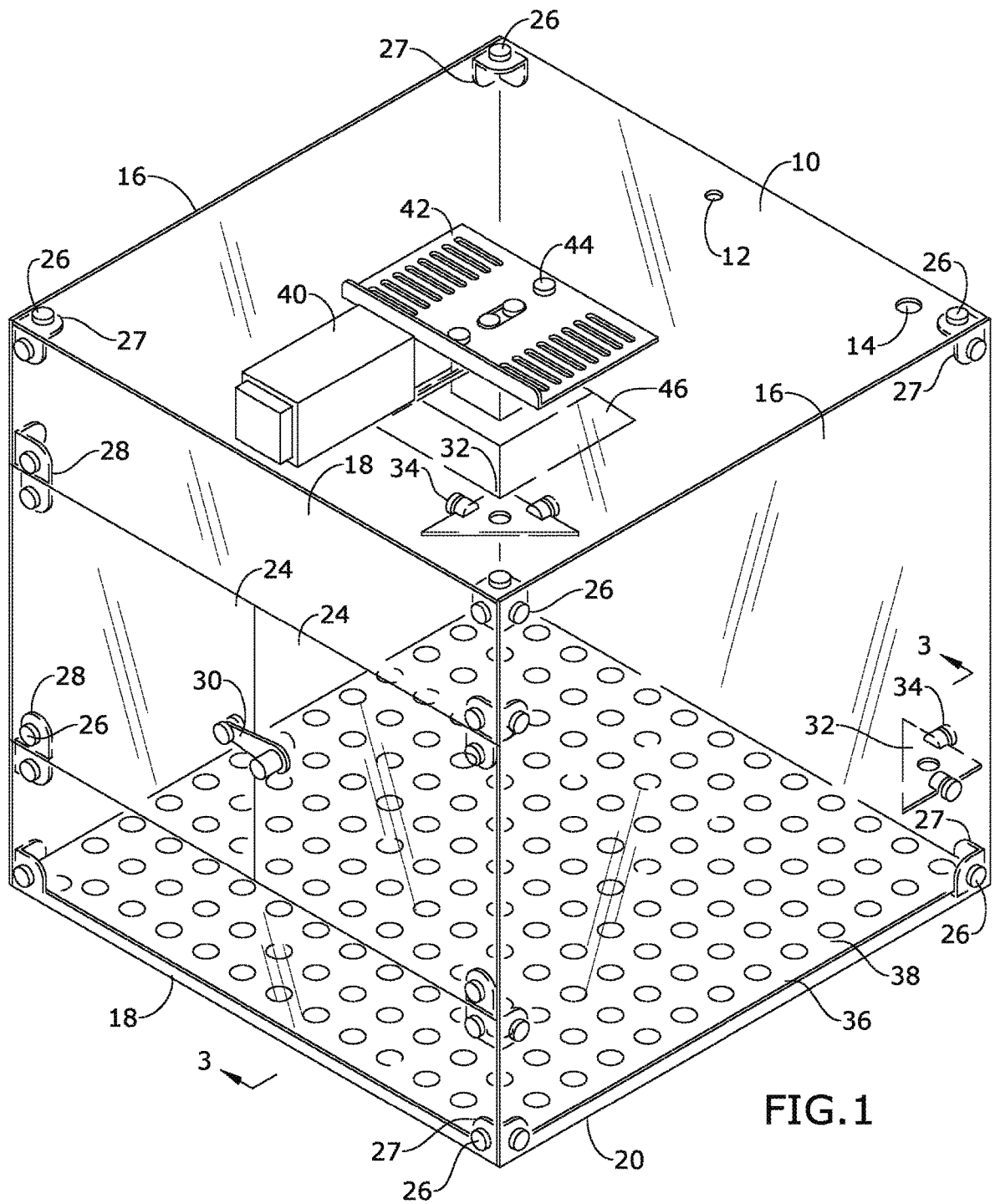
FIG. 1 is a perspective view of a modular microclimate veterinary incubator.
Figure 2:
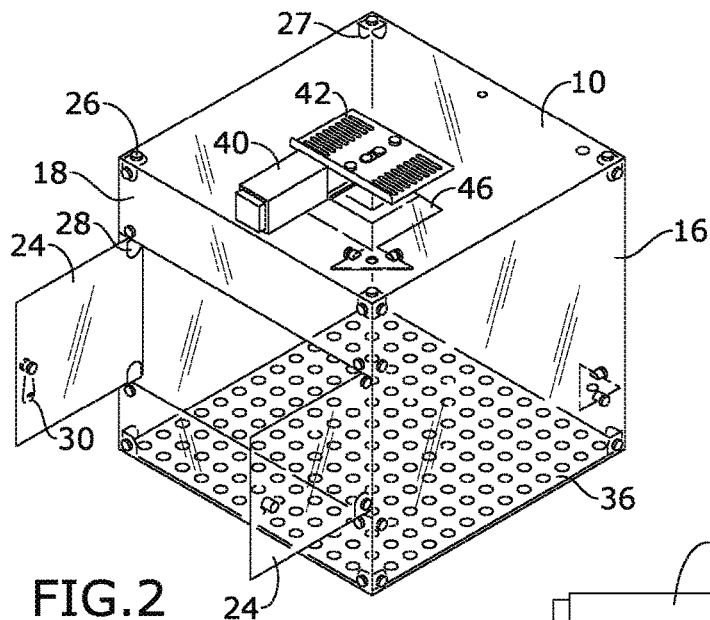
FIG. 2 is a perspective view of the modular microclimate veterinary incubator, shown with doors 24 in an opened condition.
Figure 3:
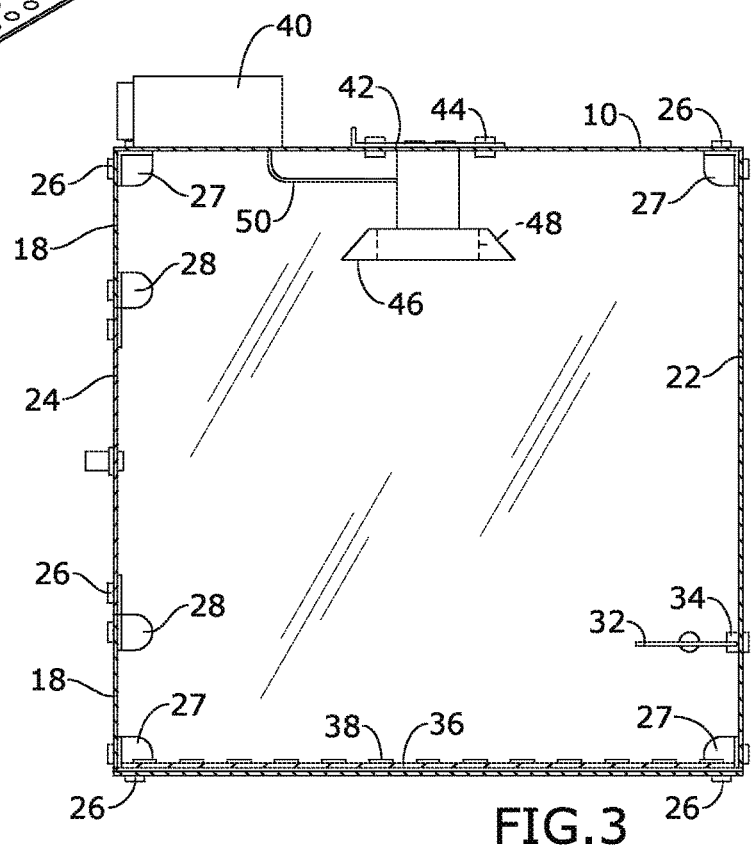
FIG. 3 is a section view of the modular microclimate veterinary incubator, taken along line 3-3 in FIG. 1.
Figure 4:
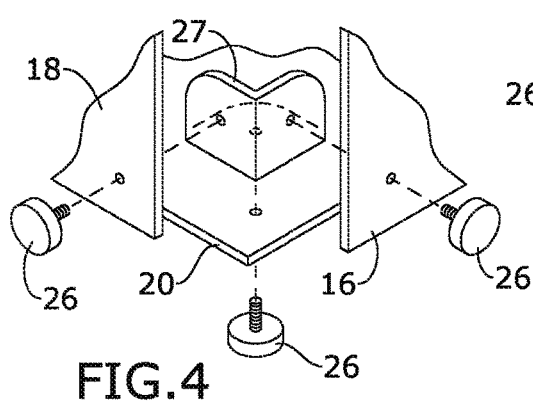
FIG. 4 is a detail view of a corner bracket and a joining a corner of the tempered glass panels.
Figure 5:
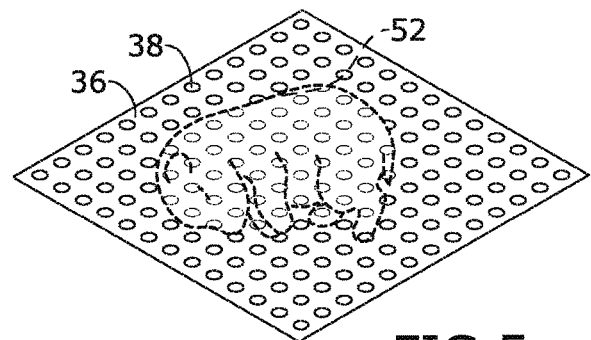
FIG. 5 is a perspective view of the thermal mat 36 encouraging puppy 52 to sleep on its side and back.

The following detailed description is of the best currently contemplated modes of carrying out exemplary embodiments of the invention. The description is not to be taken in a limiting sense but is made merely for the purpose of illustrating the general principles of the invention.

Broadly, embodiments of the present invention provides a system, method, and apparatus for providing a controlled micro climate veterinary incubator.

As seen in reference to the drawings of FIGS. 1-7, a modular microclimate veterinary incubator the present invention provides a partially closed system comprised of a plurality of tempered glass panels 10, 16, 18, 20, 22, 24 joined in a desired configuration by a plurality of fasteners 26 and a plurality of corner brackets 27. The tempered glass panels provide strength and thermal resistance to the enclosure and visibility of a puppy 52, or other young animal, contained within the enclosure. The plurality of tempered glass are non-porous allows for an unprecedented level of disinfection for a veterinary care incubator. The thermal properties of the plurality of tempered glass panels permit the creation of a thermal gradient within the enclosure. Modular construction allows the incubator to be fully disassembled resulting in flat fully exposed non-porous surfaces to clean and disinfect. Further, the modular design allows for safer, more cost effective shipping and the elimination of the need for service calls.

The plurality of tempered glass panels include a top panel 10, a side panel 16, a front fixed panel 18, a bottom panel 20, a rear panel 22, and a door panel 24. In the embodiments of FIGS. 1-6, the plurality of sidewalls 10, 18, 20, 22, 24 are joined to form a rectangular enclosure defining an incubator chamber therein. For the rectangular enclosure plurality of corner brackets 27 include three orthogonally aligned faces defining a corner of a rectangle. An aperture is defined through each of the three orthogonally aligned faces for receiving the fastener 26.

The front panel 18 may be arranged to define a fenestration with at least one door panel 24 that is attached with a hinge 28 to provide a closure for the fenestration. In the embodiment shown in FIGS. 1-5, the front panel 18 may include a top front panel 18 and a bottom front panel 18, with the fenestration defined between the top front panel 18 and the bottom front panel 18. In the embodiment shown in FIG. 6, the fenestration is shown above a bottom front panel 62, and below the top panel 60, with door panels 64 providing the closure for the fenestration. The door panels 24, 54, 64, 84, may include a latch 30 to retain the at least one door panel in a closed condition. The fenestration provides access to the incubator chamber.

Figure 6:
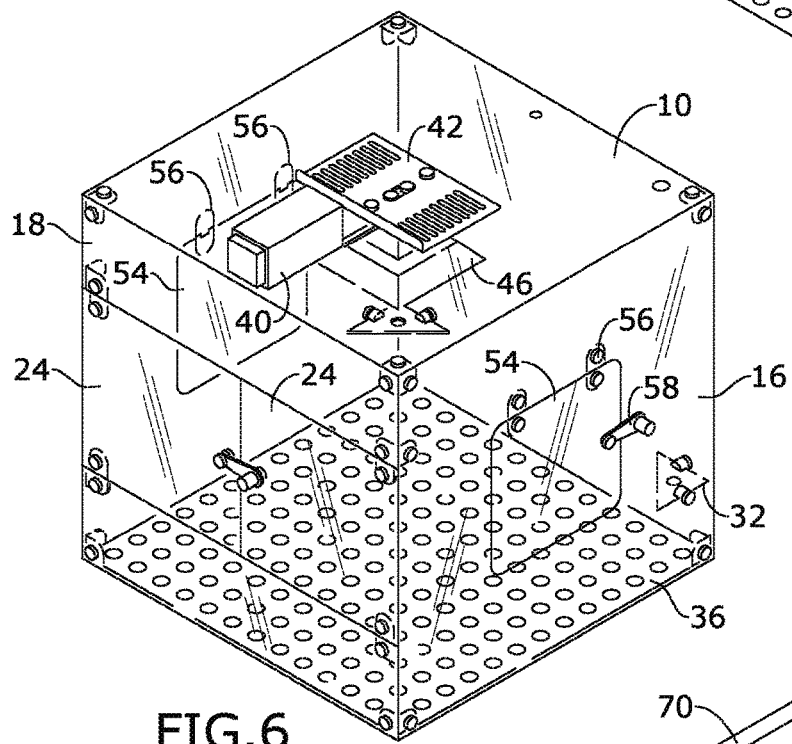
FIG. 6 is a perspective view of an alternate embodiment of the modular microclimate veterinary incubator with a secondary access fenestration and access panel.

In the embodiment shown in FIG. 6, the side panel 16 may include a secondary fenestration with an access panel 54 covering the secondary fenestration. The access panel 54 is attached to the side panel 16 with a hinge 56 and secured with a latch 58.

Figure 7:
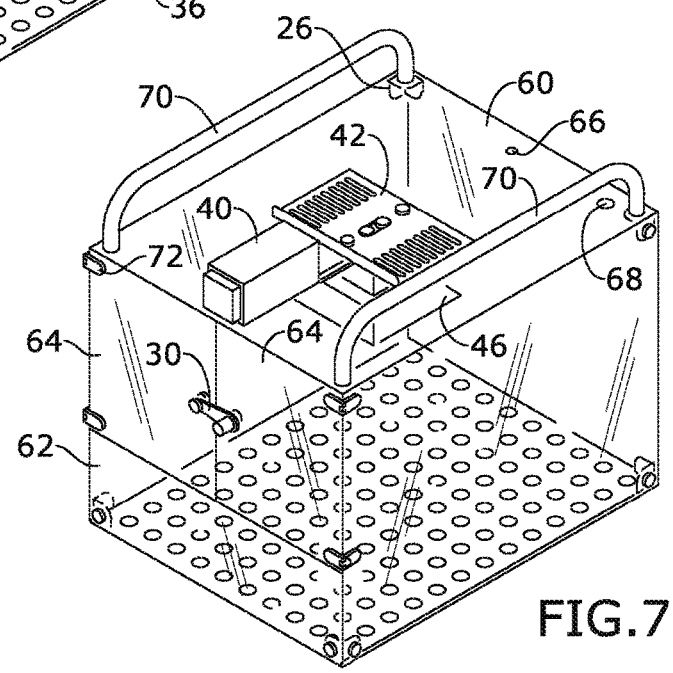
FIG. 7 is a perspective view of an alternate embodiment of the modular microclimate veterinary incubator showing transport and handling rails.
Figure 8:
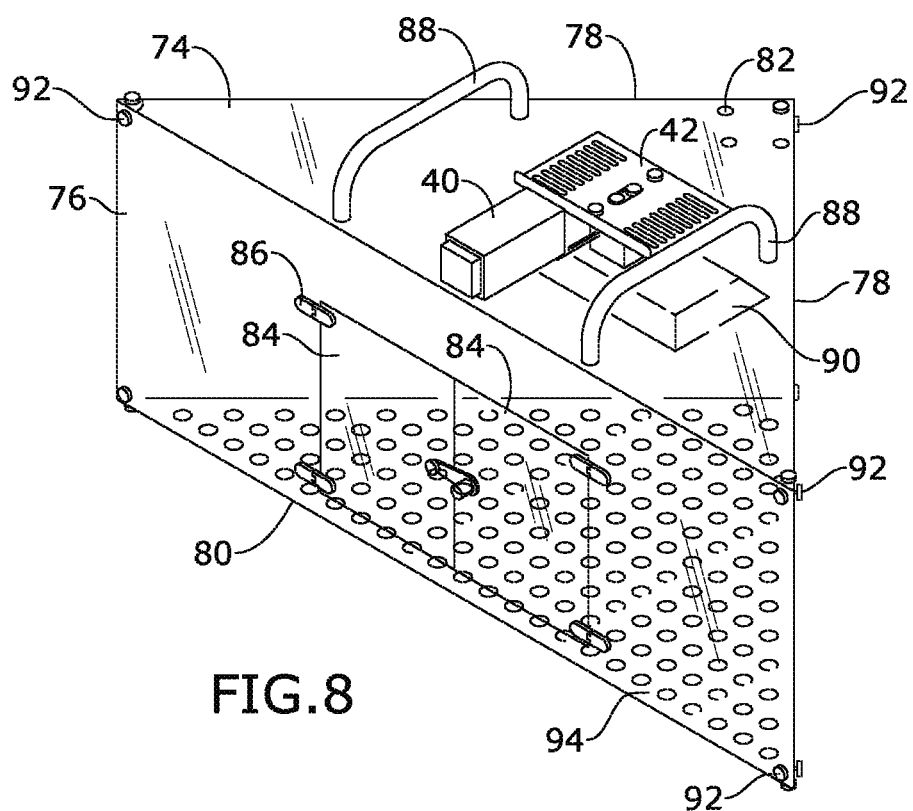
FIG. 8 is a perspective view of an alternate embodiment of the modular microclimate veterinary incubator in a corner configuration.

In the embodiment shown in FIG. 7, the front panel 76 surrounds the fenestration and door panels 84 provide the closure to the fenestration. In this embodiment, the top panel 74 and bottom panel 80 are triangular in shape so as to fit within a corner of a room, pen, or stall in which the modular micro-climate veterinary incubator will be housed.

The micro-climate veterinary incubator includes a heating element 48. The heating element 48 is mounted to an interior surface of the top panel 10. A reflective shroud 46 surrounds the heating element 48 and is configured with a focal length to project the heat towards a thermal mat 36 mounted at a bottom of the interior of the micro-climate veterinary incubator. The focal length is oriented to create a thermal gradient on the surface of the thermal mat 36. The heating element 48 is mounted to the top panel 10 with one or more fasteners 44 received through apertures in the top panel 10. A wiring harness 50 connects the heating element 48 with a controller 40. The controller 40 is configured to maintain the thermal gradient on a surface of the thermal mat 36 and the air contained within the interior contained within the plurality of tempered glass panels 10, 16, 18, 20, 22, 24. Preferably, the heating element 48 comprise a ceramic infrared heating element. The heating element 48 emits medium to long range infrared radiation that heats a puppy deeper into their body tissue and results in less loss of body fluids when compared to conventional convective heat typically used in veterinary incubators. More preferably, the infrared radiation is in the range of 9-12 micrometers.

Temperature regulation for the micro-climate is provided by a controller 40 for precision control of the heating element 48 to create and maintain a thermal gradient across the surface of the thermal mat 36 and within the volume enclosed by the tempered glass panels 10, 16, 18, 20, 22, 24 that allows for a fine tuning of a microenvironment specific to a condition of the puppy. A plurality of thermal sensors 45 are disposed about the interior of the incubator to measure the temperature and provide feedback to the controller 40. The thermal sensor 45 may include a thermocouple that responds heat conditions by generating a small amount of electricity which is then interpreted by the controller 40 regulates the electricity delivered to the heating element 48.

The controller 40 may be a proportional or proportional integral derivative controller capable of regulating the electricity delivered to the heating element 48, as determined by the sensed temperature, proximity to a target set temperature and rate of rise of temperature in the microenvironment. The controller 40 may be programmed for a specific lower set limit and an upper set limit to limit the operator's choices appropriate for a primary range of temperatures for puppies 52. These limits can be reset for other animal applications.

The thermal sensor 45 may extend from one or more sidewalls and protrude into the interior to measure an air temperature about the puppy 52 on the thermal mat 36. The thermal sensor 45 may extend from the top panel 10 and be positioned to measure the temperature in the thermal gradient above the puppy 52. Preferably, in proximity to the puppy 52, but elevated so that they are inaccessible to the puppy 52 as they begin to stand on their own.

The controlled micro climate veterinary incubator of the present invention creates a thermal gradient proven to be compatible with a neonatal puppy's innate ability to seek out warmer and cooler parts of its environment to in order to regulate its internal body temperature within in an ideal range to better process colostrum and nutrition. Because, the micro climate veterinary incubator heats a puppy 52 more deeply and can be tailored to the specific condition of the puppy 52, the puppy 52 are better able to process colostrum and food—leading to a better weight gain, a stronger immune system and eyes opening sooner that competitive products with puppies from the same litter.

The heating element 48, thermal sensor 45, and controller 40 are designed in a way that the user can quickly and intuitively replace the units. The heating element 48 and controller module 40 can be replaced with commercially available hand tools, such as an Allen wrench or screwdriver. Likewise, the thermal sensor 45 is replaceable by hand at the controller 40 and can be removed from the controller module without tools. Each of the modules can be replaced in 10 minutes or less by the end user, without need for technical support or a service call.

The thermal mat 36 is supported on an upper surface of the bottom corner brackets 27. The thermal mat 36 may be formed of any suitable material to support the puppy 52 or litter of puppies within the chamber. The thermal mat 36 has a plurality of upstanding protrusions 38 disposed in a spaced apart relation about a surface of the thermal mat 36. The plurality of protrusions encourages the puppy 52 to sleep on back or side, rather than their chest to prevent an irregular chest development, and a condition often referred to a "flatchestedness."

The thermal mat 36 may be made of any suitable material and may be supported by a top surface of the corner brackets 27 at the bottom of the enclosure. Preferably, the thermal mat 36 is made of a closed cell foam material to provide a soft, water resistant thermal mass with antimicrobial properties. The thermal mat 36 is preferably in a black or other thermally receptive color to absorb radiant heat emitted by the heating element 48. The thermal mat 36 is designed to accept infrared radiation and store as heat.

The veterinary microclimate incubator operates in the following manner. The heating element 48, the thermal sensor 45, and the controller 40 are interconnected to provide a heat sensing control and delivery system capable precisely controlling the thermal gradient microenvironment. The soft, water resistant, thermal mat 36 accepts the medium to long range infrared radiation and stores the radiation as heat energy. The tempered glass enclosure has sufficient heat loss to cause the heating element 48 to have a higher duty cycle, allowing for the puppies to be heated more deeply by the infrared radiation.

The tempered glass also creates a thermal gradient where the center of the thermal mat 36 is warmer and progressively cools approaching the outer edges of the thermal mat 36 where it interfaces with the sides of the tempered glass side, front, and back panels. This creates a microenvironment where small animals can move freely within an indirectly heated thermal mass that has slightly warmer and slightly cooler locations that create a predictable pattern within the micro environment. This enables the small animal to use their ability to regulate their body temperature by moving to a location that meets their needs based on their current ability to regulate body temperature above ambient.

The creation of this micro environment will increase the survival rate of small for gestational age (SGA), gasping/oxygen deprived puppies when used in conjunction with an oxygen supply, puppies experiencing difficulty thermoregulating, premature puppies, puppies with underdeveloped lungs, and used at elevated temperatures with increase survival rate of puppies suffering from Canine Herpes Virus.

As indicated, the system works together to create a micro environment with a thermal gradient that can be tuned to specific conditions of the small animal, can be more fully disinfected. The vent 42 can be regulated to control oxygen and humidity levels while allowing carbon dioxide to escape from the microenvironment. The soft thermal mass mat 36 has upstanding protrusions 38 encourages neonatal puppies to sleep on their back and sides.

Neonatal puppies consistently interact with the thermal gradient of the system in a specific way that allows the operator to determine if the puppy 52 is at the correct internal temperature within the micro environment. If the puppies 52 are curled in a "C" or in a pile together, indicating a cold condition, the operator should raise the micro environment temperature with the controller 40 upwardly by a degree at a time until the puppy 52 lays out straighter and longer or the puppies 52 are no longer on top of each other.

If the puppy 52 is pressed against the tempered glass, its internal body temperature is too warm. This indicates that the puppy 52 is innately attempting to reduce heat to a cooler object. In this case, the controller 40 should be lowered in temperature by 1 degree increments until the puppy 52 moves away from the tempered glass.

A puppy 52 that lays out straight and long is at the correct internal temperature. A puppy 52 that lays on its back or side is a comfortable puppy 52 at the correct body temperature. A puppy 52 that actively moves between the center of the thermal gradient perimeter of the thermal gradient is fine tuning their internal body temperature. Understanding the behavior of the puppies 52 and adjusting the incubator temperature improves the ability of the puppy 52 to process food and colostrum.

The invention is assembled with the plurality of machined glass panels that are tempered after machining. The brackets and fasteners are made of a stainless-steel to mount the panels and allow for assembly and disassembly by the customer. A proportional or proportional integral derivative controller capable of regulating the electricity delivered to the heater as determined by the sensed temperature, proximity to target set temperature and rate of rise of temperature in the microenvironment. The controller may be programmed for a specific lower set limit and an upper set limit to limit the operator's choices appropriate for the primary range of temperatures for puppies. These limits can be reset for other animal applications.

Each of the components are designed to be replaced with basic supplied tools with minimal effort as a result of quick connect interconnects for power and sensing and mounting hardware that can be installed by hand and secured with Allen wrenches or similar simple tools. The mat is made of closed cell foam or a silicone-based material that has "give and grip" that allows for puppies to move easily and encourage proper hip development.

As will be appreciated it is possible to use a halogen infrared heating elements 48. However, the halogen heating elements 48 can be dangerous when they fail.

The heating element 48 of the present invention may also have an embedded insulation and has a lower watt density over the surface, shifting the infrared radiation further into the long wavelength spectrum.

The present invention will be predominantly used by Veterinarians, Veterinary Technicians, Dog Breeders, Cat Breeders, Domestic and Wildlife Rescue and Zoo staff. The user interface for the control system allows the user to modify the target temperature in a specified range. As an example, the range could be 80° F. to 100° F. In some embodiments, the only option the user has is to change the target temperature from the default, in most cases 88° F. depending on the age and assessment of the puppy or small animal neonate.

The system may also be used in conjunction with an oxygen concentrator which can also be used to augment an oxygen content within the enclosure. Optional humidity introduction devices may also be provided to regulate the humidity within the enclosure. The ability to precisely control heat, humidity, and oxygen provides an optimal microenvironment for saving at risk puppies. The thermal gradient creates a microenvironment that is suitable for all puppies in a litter with significant size and body fat variance.

A corner bracket 32 may be secured by a fastener 34. The corner bracket has an aperture to receive oxygen in a more concentrated delivery method.

Veterinarians have found that puppies feed better coming out of a C-section, when the microclimate veterinary incubator of the present invention is used. The first three to four feedings are essential to building a stronger immune system. For proper processing of colostrum, the puppy's internal body temperature must be above 95 degrees F. Puppies born gasping, without the assistance of an oxygen rich environment, are likely to have a smaller window of opportunity to process colostrum. An oxygen rich environment extends the window of opportunity for a gasping puppy.

Additionally, the present invention may be used in other veterinary and animal husbandry applications. For example, could be used to hatch reptile eggs, treat adult animals experiencing difficult thermoregulation, and as a chamber for oxygen therapy or nebulization.

It should be understood, of course, that the foregoing relates to exemplary embodiments of the invention and that modifications may be made without departing from the spirit and scope of the invention as set forth in the following claims.

What is claimed is:

1. A microclimate veterinary incubator, comprising:
a unitary incubator enclosure, consisting of multiple tempered glass panels dimensioned to form the unitary incubator enclosure, a plurality of corner brackets, join and retain the multiple tempered glass panels as the unitary incubator enclosure, a thermal mat spanning a bottom of the unitary incubator enclosure, the thermal mat having a surface to capture a thermal radiation;
a ceramic infrared heating element coupled within the unitary incubator enclosure and emit an infrared heat source in the range of 9-12 micrometers; and
a reflective shroud surrounds the ceramic infrared heating element, the reflective shroud having a focal length to orient the infrared heat source onto the surface of the thermal mat to define a thermal gradient on the surface of the thermal mat and an airspace above the thermal mat, the thermal gradient defining a microenvironment having a warmer center portion that progressively cools approaching a peripheral outer edge of the thermal gradient proximal with one or more of the multiple tempered glass sidewalls, wherein a small animal can move freely within the thermal gradient microenvironment.

2. The microclimate veterinary incubator of claim 1, further comprising:
a controller configured to control the heating element to maintain the thermal gradient at a desired set point.

3. The microclimate veterinary incubator of claim 1, further comprising:
at least one thermal sensor configured to be coupled to one or more of the tempered glass panels and oriented to measure a temperature of the airspace above the thermal mat, the at least one thermal sensor configured to be operably coupled to the controller.

4. The microclimate veterinary incubator of claim 1, further comprising:
a plurality of upstanding protrusions defined on an upper surface of the thermal mat in a spaced apart pattern spanning the upper surface of the thermal mat.

5. The microclimate veterinary incubator of claim 1, wherein each corner bracket comprises
three orthogonal faces defining a corner of a regular rectangular solid; and
an aperture defined in each of the three orthogonal faces.

6. The microclimate veterinary incubator of claim 1, wherein the tempered glass panels comprise:
a top panel, a bottom panel, at least two side panels, a rear panel, and a front panel.

7. The microclimate veterinary incubator of claim 6, wherein the front panel further comprises: a fenestration and a door panel movable to close the fenestration.

8. The microclimate veterinary incubator of claim 6, wherein the at least two side panels further comprises:
a fenestration, and
an access panel operable to close the fenestration.

9. A microclimate veterinary incubator, comprising:
a unitary incubator enclosure consisting of a plurality of tempered glass panels including a top panel, a bottom panel, a front panel, a rear panel, and at least two side panels, a plurality of corner brackets join and retain the plurality of tempered glass panels of the unitary incubator enclosure, and a thermal mat supported at bottom of the unitary incubator enclosure spanning between the front panel, the rear panel, and the at least two side panels, the thermal mat having a surface to capture a thermal radiation;
a ceramic infrared heating element removably attached to the top panel and extending into an interior of the unitary incubator enclosure; and
a reflective shroud surrounding the heating element, the reflective shroud having a focal length oriented to project an infrared heat generated by the ceramic infrared heating element onto the surface of the thermal mat to define a thermal gradient on the surface of the thermal mat and an airspace above the thermal mat, wherein a center of the thermal gradient is warmer and progressively cools approaching an outer edge of the thermal gradient where the thermal mat interfaces with the front panel, the rear panel, and the at least two side panels.

10. The microclimate veterinary incubator of claim 9, further comprising:
a controller configured to control the heating element to maintain the thermal gradient at a desired temperature set point.

11. The microclimate veterinary incubator of claim 10, further comprising:
a plurality of thermal sensors coupled to one or more of the plurality of tempered glass panels and oriented to measure a temperature of the airspace above the thermal mat, the plurality of thermal sensors operably coupled to the controller.

12. The microclimate veterinary incubator of claim 9, further comprising:
a plurality of upstanding protrusions defined on an upper surface of the thermal mat in a spaced apart pattern spanning the upper surface of the thermal mat.

13. The microclimate veterinary incubator of claim 9, wherein the front panel further comprises: a fenestration and a door panel movable to close the fenestration.

14. The microclimate veterinary incubator of claim 9, wherein the at least two side panels further comprises:
a fenestration, and
an access panel operable to close the fenestration.

* * * * *